United States Patent [19]

Bazan

[11] Patent Number: 5,449,092
[45] Date of Patent: Sep. 12, 1995

[54] TOOTHPASTE AND FLOSS DISPENSER

[76] Inventor: Ronald R. Bazan, 6500 60th St., SE., Grand Rapids, Mich. 49512

[21] Appl. No.: 234,648

[22] Filed: Apr. 28, 1994

[51] Int. Cl.⁶ .............................................. B65D 35/24
[52] U.S. Cl. ..................................... 222/93; 132/325; 222/100; 222/154; 222/192; 222/181.2
[58] Field of Search .................. 222/80, 93, 95, 99, 222/100, 154, 156, 181, 192; 132/324, 325

[56] References Cited

U.S. PATENT DOCUMENTS

| | | |
|---|---|---|
| D. 124,707 | 1/1941 | Baumeister . |
| D. 217,263 | 4/1970 | Manning ................... D6/1 |
| D. 227,836 | 7/1973 | Roiko ....................... D6/6 |
| 1,117,208 | 11/1914 | Mars ....................... 222/100 |
| 1,143,390 | 6/1915 | Heideloff ............... 222/100 |
| 1,432,644 | 10/1922 | Uber ...................... 222/100 |
| 1,439,076 | 12/1922 | Edwards ................. 222/93 |
| 1,481,236 | 1/1924 | Spine ..................... 222/100 |
| 1,487,215 | 3/1924 | Dial ........................ 222/99 |
| 1,563,459 | 12/1925 | Volland . |
| 1,568,868 | 1/1926 | Blackmon .............. 222/100 |
| 1,603,764 | 10/1926 | Gudmundsen ......... 222/100 |
| 1,631,275 | 6/1927 | Leake .................... 222/100 |
| 1,644,145 | 10/1927 | Perkins ................. 222/100 |
| 1,747,590 | 2/1930 | McCorkindale ....... 222/100 |
| 1,813,457 | 7/1931 | Lodge ................... 222/100 |
| 1,839,079 | 12/1931 | Behm .................... 222/100 |
| 1,839,542 | 1/1932 | Ferguson ........... 222/100 X |
| 1,858,134 | 5/1932 | Booth .................... 222/93 |
| 1,873,217 | 8/1932 | Reid . |
| 1,895,163 | 1/1933 | Johnson ............. 222/100 X |
| 1,904,050 | 4/1933 | Jaedike ................. 222/101 |
| 1,912,944 | 6/1933 | Lee .................... 222/100 X |
| 1,978,798 | 10/1934 | Kirmss .................. 221/60 |
| 1,979,517 | 11/1934 | Wohlfeld .............. 221/60 |
| 2,016,357 | 10/1935 | Andrews ............... 222/100 |
| 2,060,178 | 11/1936 | Crumm ................. 221/60 |
| 2,097,308 | 10/1937 | Ruth ..................... 221/60 |
| 2,183,060 | 12/1939 | Blake .................... 221/60 |
| 2,251,574 | 8/1941 | O'Neill .................. 221/60 |
| 2,507,651 | 5/1950 | Small ..................... 222/100 |
| 2,530,476 | 11/1950 | Morris .................. 222/100 |
| 2,542,678 | 2/1951 | Keefer ................... 222/98 |
| 2,548,535 | 4/1951 | Iannone ................ 222/98 |
| 2,708,532 | 5/1955 | Tarbox ................. 222/100 |
| 2,715,979 | 8/1955 | Leonard ............... 222/101 |
| 3,173,578 | 3/1965 | Williams ............... 222/93 |
| 3,204,824 | 9/1965 | McGraw, Jr. ......... 222/100 |
| 3,241,721 | 3/1966 | Freeman ............... 222/93 |
| 3,917,118 | 11/1975 | Odgen ................... 222/101 |
| 4,010,871 | 3/1977 | Broadie ................ 222/93 |
| 4,220,260 | 9/1980 | Webster ............... 222/100 |
| 4,428,389 | 1/1984 | Cordero ................ 132/92 |
| 4,508,239 | 4/1985 | Rozzen ................. 222/39 |
| 4,570,829 | 2/1986 | Allen ..................... 222/181 |
| 4,796,783 | 1/1989 | Paulson ................ 222/80 |
| 4,827,951 | 5/1989 | Grussmark ........... 132/314 |
| 4,934,389 | 6/1990 | Pettiford .............. 132/325 |
| 5,048,725 | 9/1991 | Peterson .............. 222/100 |
| 5,145,095 | 9/1992 | Loudon ................. 222/181 |
| 5,277,332 | 1/1994 | Rogers .............. 222/100 X |

FOREIGN PATENT DOCUMENTS 2068897  8/1981  United Kingdom ............... 222/156

*Primary Examiner*—Andres Kashnikow
*Assistant Examiner*—Joseph A. Kaufman
*Attorney, Agent, or Firm*—Price, Heneveld, Cooper, DeWitt & Litton

[57] ABSTRACT

A toothpaste and floss dispenser having an elongated guide body with opposite ends, the guide body defining a dental floss chamber therein, a pair of mounts spaced from each other and attached to the guide body adjacent respective ones of the guide body ends, the mounts having securing portions for adhering the mounts to a wall surface, a guide follower having a sliding interfit with the guide body for movement along the guide body between the mounts, the guide follower having rotational toothpaste tube gripping and winding spool for winding a toothpaste tube thereon to dispense toothpaste from the tube. One of the mounts has a dental floss dispensing passage in communication with the dental floss chamber of the guide body and with the exterior, and a floss cutter.

10 Claims, 4 Drawing Sheets

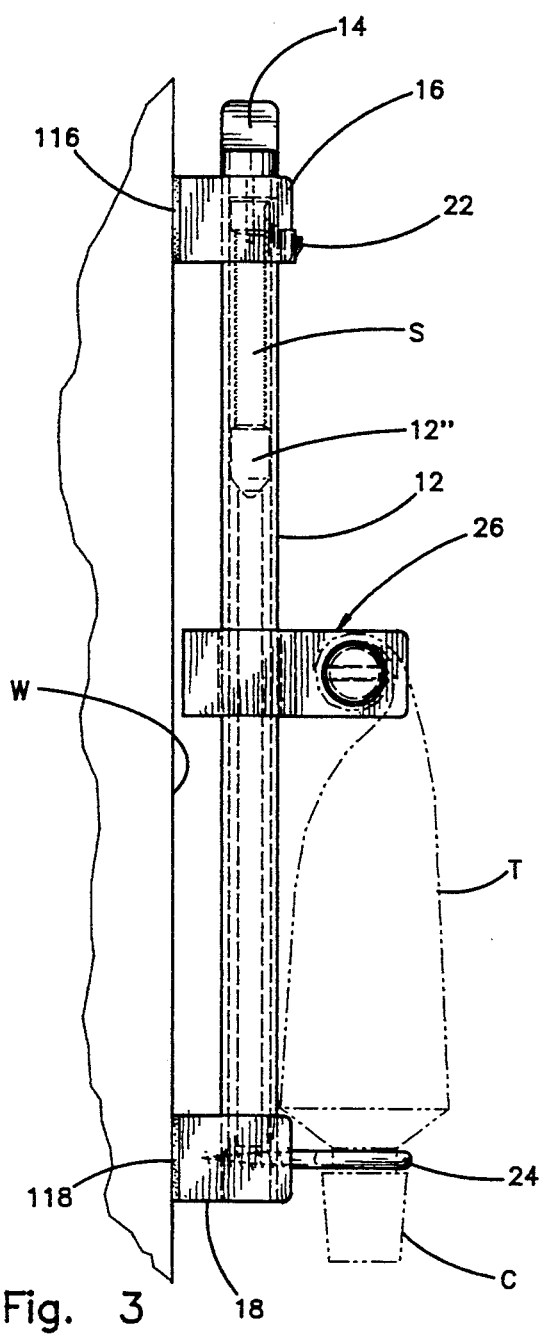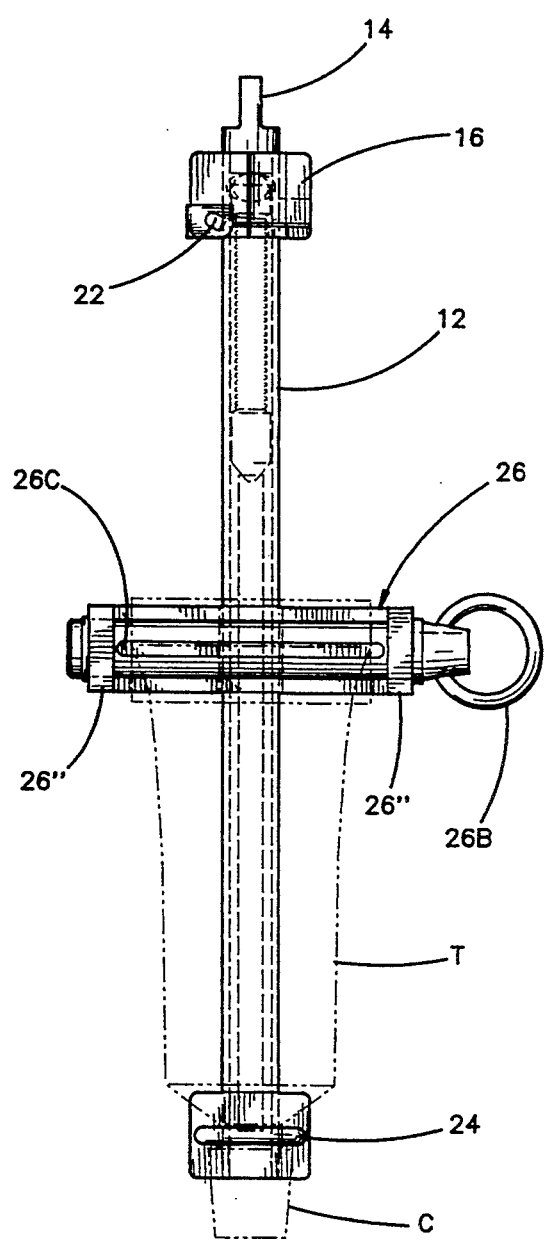
Fig. 3
Fig. 4

TOOTHPASTE AND FLOSS DISPENSER

BACKGROUND OF THE INVENTION

This invention relates to a unique combination toothpaste and dental floss dispenser.

Devices for dispensing toothpaste have been known heretofore, see, e.g., U.S. Pat. Nos. 1,117,208; 1,143,390; 1,432,644; 1,481,236; 1,563,459; 1,568,868; 1,603,764; 1,631,275; 1,644,145; 1,747,590; 1,813,457; 1,839,079; 1,839,542; 1,873,217; 1,895,163; 1,904,050; 1,912,944; 1,978,798; 1,979,517; 2,060,178; 2,097,308; 2,183,060; D. 124,707; 2,25 1,574; 2,507,65 1; 2,530,476; 2,542,678; 2,548,535; 2,708,532; 3,173,578; 3,241,721; D.217,263; D.227,836; 3,917,118; 4,010,871; 4,220,260; and 5,048,725. Dental floss dispensers are typically of the box or cartridge types, although floss dispensers with a toothpaste tube or dispenser are shown in U.S. Pat. Nos. 1,439,076; 1,487,215; 1,858,134; 2,016,357; 2,715,979; 4,428,389; 4,508,239; 4,796,783; 4,827,951 and 4,934,389.

SUMMARY OF THE INVENTION

An object of this invention is to provide a unique wall mount dispenser which has components that serve a plurality of functions, to thereby be capable of dispensing toothpaste and dispensing dental floss. The device has an elongated guide body that guides the toothpaste tube winder and also houses dental floss. The guide body is supported on a pair of mounts, one of which has a dental floss passage from the floss chamber for discharge of floss to the exterior, and has a floss cutter.

The wall mount dispenser is capable of manufacture at a reasonable cost, is attractive, and has transparent guide body and mount members enabling visual observation of the floss in the chamber and in the one mount.

These and other objects, advantages and features of the invention will become apparent upon studying the following specification in conjunction with the drawings.

BRIEF DESCRIPTION OF THE DRAWINGS

FIG. 3 is a side elevational view of a second embodiment of the invention;

FIG. 4 is a front elevational view of the second embodiment; and

DESCRIPTION OF THE PREFERRED EMBODIMENTS

Figure 1:
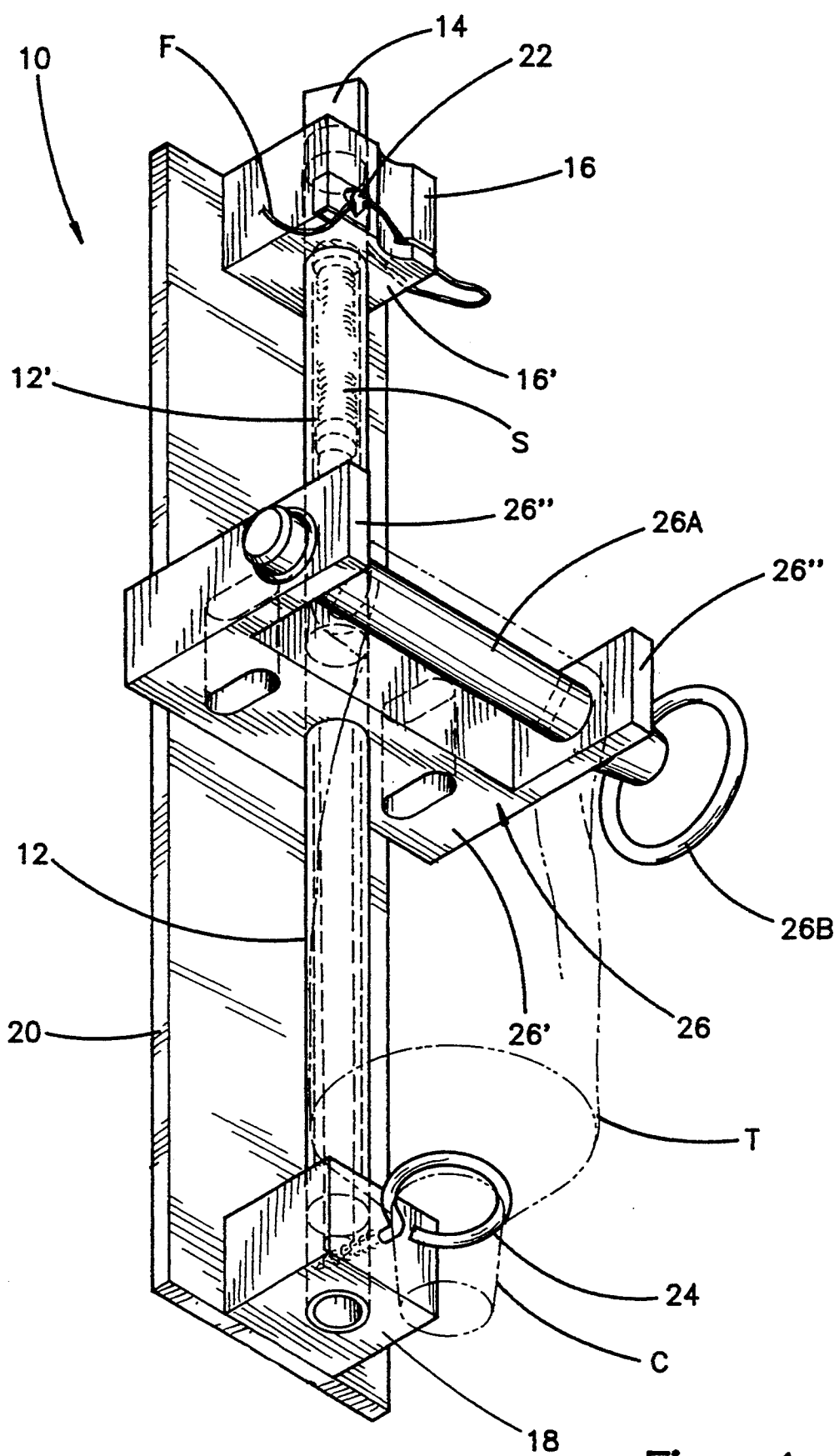
FIG. 1 is a perspective view of one embodiment of the invention.
Figure 2:
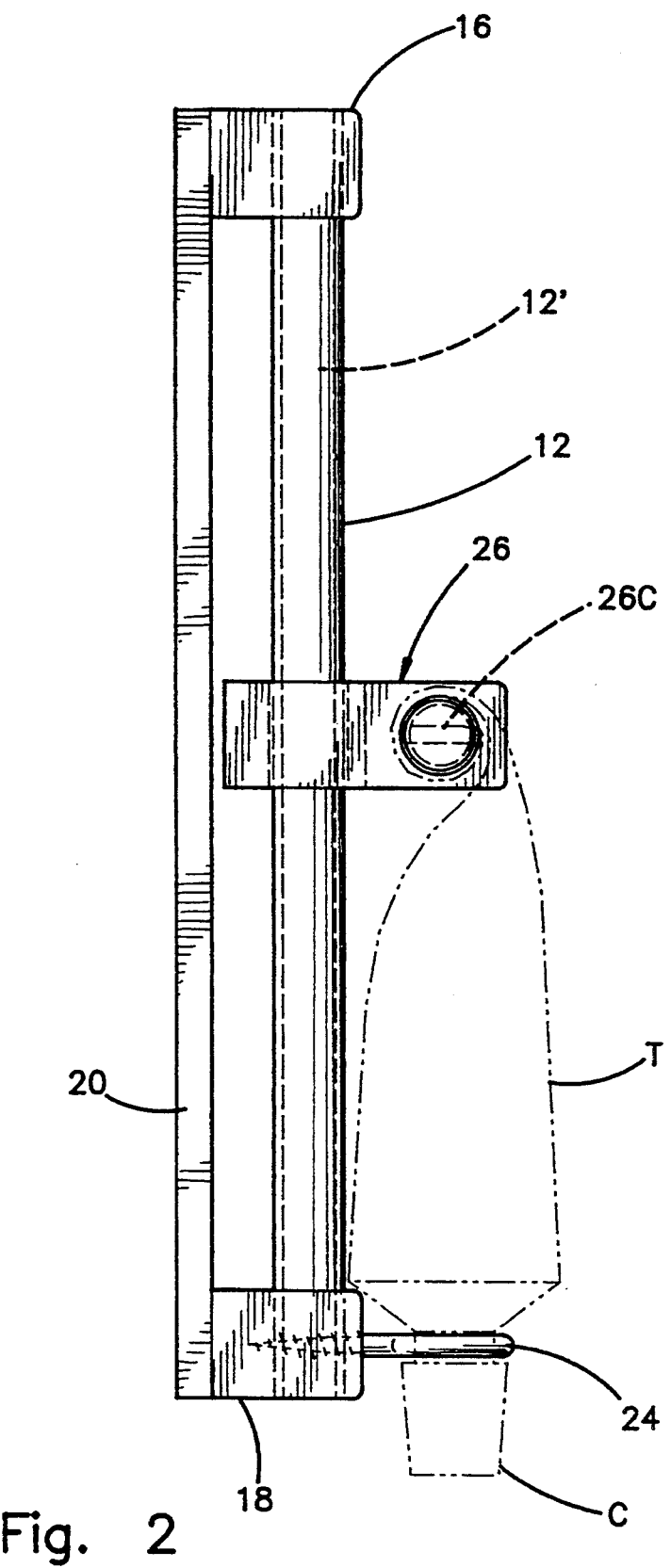
FIG. 2 is a side elevational view of the embodiment in FIG. 1.

Referring first to FIGS. 1-2, the apparatus 10 there depicted includes an elongated guide body 12 which is here shown to be generally cylindrical in cross section, and having opposite ends. This guide body is hollow, and shown to be formed of a transparent polymeric or glass material to define an internal chamber 12' which constitutes a floss retention chamber. The lower end of the chamber is plugged or closed while the upper end includes a removable closure 14 such as a plug or cap. This elongated guide body is supported by and attached to a pair of upper and lower mounts 16 and 18 which, in embodiment one, are shown to be integrally attached to a back plate 20. Back plate 20 has a back surface which can be attached to a wall surface as by any suitable means such as adhesive, fasteners such as screws, or the like. Mounts 16 and 18 are also preferably of a transparent material such as a transparent polymer. One of the mounts, such upper mount 16, is shown to have a passageway 16' therethrough which communicates with chamber 12' in body 12 for extension of dental floss F from the chamber through mount to the exterior thereof. A floss cutter 22 is attached to the outside of mount 16 for cutting a length of floss as desired. A spool S of floss can be retained in chamber 12' so that the floss F can be withdrawn and cut as needed. Lower mount 18 is shown to have a receiver 24 attached thereto for receiving the discharge end and neck of a toothpaste tube T. The tube can be retained in this receiver by reattachment of the cap C after the neck of the tube is placed therein.

A toothpaste tube winder 26 has a cylindrical opening through its slide element 26' for receiving elongated guide body 12, being slidable therealong as a guide follower to move between the two mounts 16 and 18 as the toothpaste tube is wound. The winder includes a pair of laterally protruding, spaced, parallel flanges 26" on slide element 26'. A windup spool 26A extends through these two flanges and has a small, finger-actuable handle 26B on one end thereof. Winder spool 26A is rotational relative to flanges 26" and preferably has a central slot 26C (FIG. 2) therethrough for receiving the end of the toothpaste tube opposite the cap C. Rotation of spool 26A will wind up the tube while the winder 26 is moved along body 12.

Figure 5:
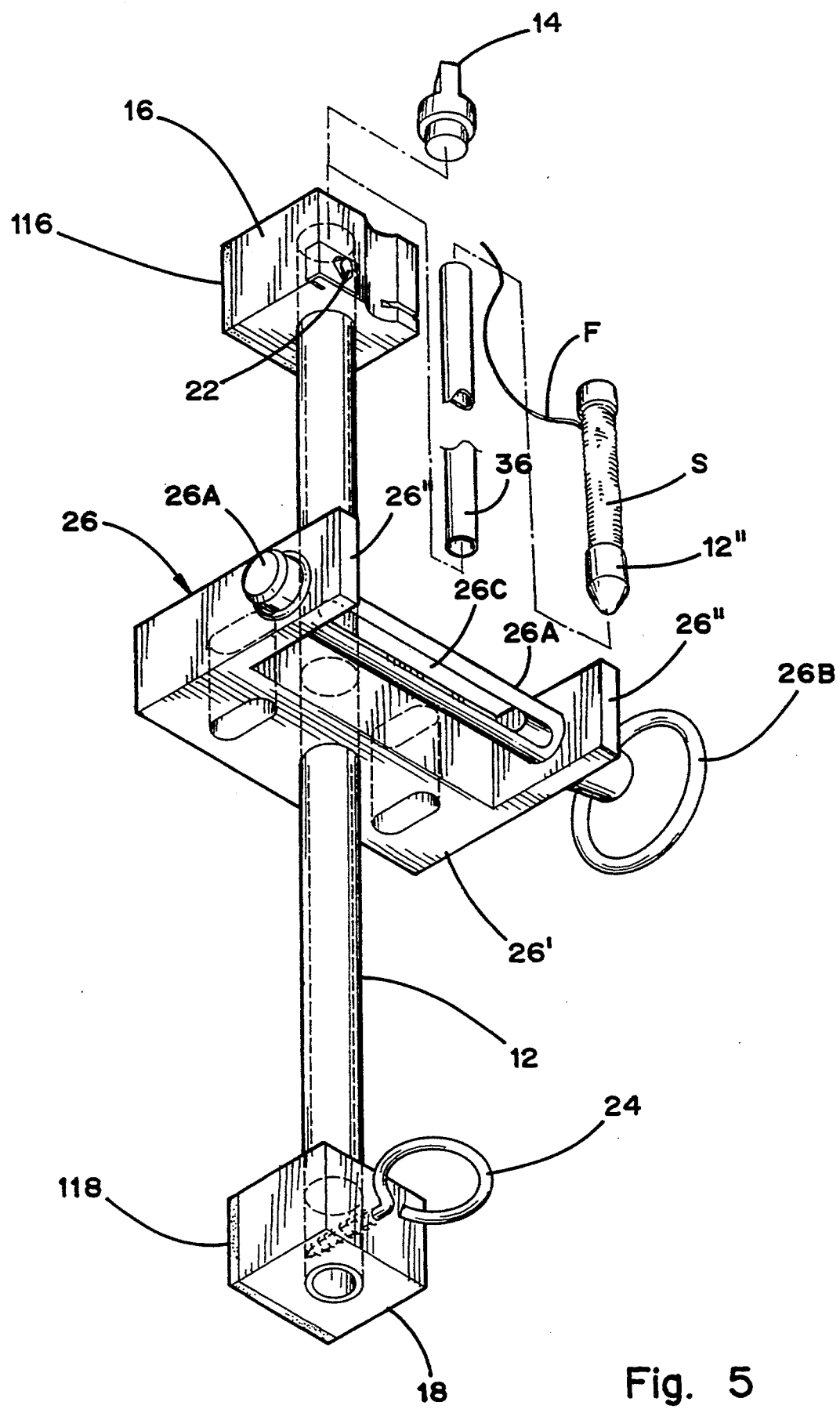
FIG. 5 is a fragmentary, exploded, partial perspective view of the second embodiment.

The second embodiment depicted in FIGS. 3, 4 and 5 has elements common to both embodiments. Therefore, for purposes of clarity, the same numerals on FIGS. 3, 4 and 5 are used to refer to the same elements. In this embodiment, however, the mounts 16 and 18 are shown to include a layer of double faced adhesive 116 and 118 respectively for attachment directly to the surface of a wall W. In this second embodiment, the spool S of floss is shown retained in the upper end of chamber 12' of body 12 by a suitable interior stop 12".

Optionally, an advertising or identification cylinder 36 (FIG. 5) may be inserted into the lower portion of tile hollow body 12 for promotional or trademark identification purposes (FIG. 5).

As will be apparent from the above description and the drawings, the novel apparatus not only is capable of dispensing toothpaste and/or floss, but certain components of the apparatus perform a plurality of functions. Thus, guide body 12 not only supports and guides the tube winder assembly 26, but also serves as the defining chamber for dental floss. Similarly, upper mount 16 not only serves to support body 12, but also serves to allow exit of the floss from the chamber to the exterior.

It is conceivable that certain features of the apparatus may be modified without departing from the invention set forth, for example the exact exit location of the floss, the location of the floss cutter, the shape and size of the floss spool, and the like. Therefore, the invention is not intended to be limited to the specific preferred embodiments set forth as exemplary of the invention, but only by the scope of the appended claims and the reasonably equivalent structures to those defined therein.

The embodiments of the invention in which an exclusive property or privilege is claimed are defined as follows:

1. A toothpaste and floss dispenser comprising:

an elongated guide body having opposite ends, said guide body defining a dental floss chamber therein;

a pair of mounts spaced from each other and attached to said guide body adjacent respective ones of said guide body ends, said mounts having means for securing said mounts to a wall surface;

a guide follower having a sliding interfit with said guide body for movement along said guide body between said mounts, said guide follower having a rotational toothpaste tube winding spool for winding a toothpaste tube thereon to dispense toothpaste from the tube;

one of said mounts having a dental floss dispensing passage in communication with said dental floss chamber of said guide body and with the exterior, and having a floss cutter.

2. The toothpaste and floss dispenser in claim 1 wherein one of said mounts has a receiver for a conventional outlet neck of a toothpaste tube.

3. The toothpaste and floss dispenser in claim 1 wherein said guide body is transparent for viewing of floss in said floss chamber.

4. The toothpaste and floss dispenser in claim 3 wherein said one mount having said floss dispensing passage is transparent for viewing of floss therein.

5. The toothpaste and floss dispenser in claim 1 wherein said gripping and winding spool has a winding handle.

6. The toothpaste and floss dispenser in claim 1 wherein said guide body has a removable end closure for selected opening and refilling of said floss chamber.

7. A toothpaste and floss dispenser comprising:

an elongated guide body having opposite ends, said guide body defining a dental floss chamber therein and a chamber closure element for selected filling of said dental floss chamber;

a dental floss dispensing passage in communication with said dental floss chamber of said guide body and with the exterior, and a floss cutter;

a pair of mounts spaced from each other and attached to said guide body adjacent respective ones of said guide body ends, said mounts having means for securing said mounts to a wall surface; and a guide follower having a sliding interfit with said guide body for movement along said guide body between said mounts, said guide follower having a rotational toothpaste tube winding spool for winding a toothpaste tube thereon to dispense toothpaste from the tube.

8. The toothpaste and floss dispenser in claim 7 wherein said mounts are attached to a back plate for securement to a wall surface.

9. The toothpaste and floss dispenser in claim 7 wherein said mounts have adhesive backing layers for securement to a wall surface.

10. The toothpaste and floss dispenser in claim 7 wherein said guide body is transparent for viewing of floss therein.

* * * * *

UNITED STATES PATENT AND TRADEMARK OFFICE
CERTIFICATE OF CORRECTION

PATENT NO. : 5,449,092
DATED : September 12, 1995
INVENTOR(S) : Ronald R. Bazan

It is certified that error appears in the above-indentified patent and that said Letters Patent is hereby corrected as shown below:

Column 2, line 7;
    After "mount" insert -- 16 --;

Column 2, line 44;
    "tile hollow" should be -- the hollow --.

Signed and Sealed this

Fourth Day of June, 1996

Attest:

BRUCE LEHMAN

*Attesting Officer*      *Commissioner of Patents and Trademarks*